United States Patent [19]

Telschow

[11] Patent Number: 5,008,458
[45] Date of Patent: Apr. 16, 1991

[54] PROCESS FOR PURIFYING CRUDE TETRABROMOBISPHENOL SULFONE BY EXTRACTION

[75] Inventor: Jeffrey E. Telschow, Tarrytown, N.Y.

[73] Assignee: Akzo nv, Arnhem, Netherlands

[21] Appl. No.: 452,868

[22] Filed: Dec. 19, 1989

Related U.S. Application Data

[63] Continuation-in-part of Ser. No. 299,495, Jan. 23, 1989.

[51] Int. Cl.$^5$ .............................................. C07C 315/06
[52] U.S. Cl. .......................................... 568/28; 568/33; 568/724
[58] Field of Search ..................... 568/724, 28, 33, 34, 568/722

[56] References Cited

U.S. PATENT DOCUMENTS

| | | | |
|---|---|---|---|
| 3,277,183 | 10/1966 | Heller et al. ......................... | 568/724 |
| 3,794,729 | 2/1974 | Wohl et al. .......................... | 424/337 |
| 4,006,118 | 2/1977 | Ogawa et al. ......................... | 568/33 |
| 4,287,366 | 9/1981 | Yamaguchi et al. .................... | 568/33 |
| 4,291,177 | 9/1981 | Mark et al. ........................... | 568/33 |
| 4,320,234 | 3/1982 | Mark et al. ........................... | 568/33 |
| 4,414,422 | 11/1983 | Ash et al. ............................. | 568/724 |

FOREIGN PATENT DOCUMENTS

| | | | |
|---|---|---|---|
| 0211140 | 2/1987 | European Pat. Off. .............. | 568/33 |
| 0279387 | 8/1988 | European Pat. Off. .............. | 568/33 |
| 0039044 | 3/1979 | Japan .................................... | 568/33 |
| 0119430 | 9/1979 | Japan .................................... | 568/33 |

OTHER PUBLICATIONS

Sato et al "Chemical Abstracts," vol. 92 (1980) 11064b.
Hooker Chemical "Derwent Belgian Patent Report" Vol. 61, A, p. A12 Jan. 31, 1960.

*Primary Examiner*—Werren B. Lone
*Attorney, Agent, or Firm*—Richard P. Fennelly; Louis A. Morris

[57] ABSTRACT

Crude tetrabromobisphenol S compositions can be purified by extracting impurities therefrom with a quantity of organic solvent which is insufficient to substantially dissolve the tetrabromobisphenol S, followed by the removal of the tetrabromobisphenol compound from the solvent.

11 Claims, No Drawings

PROCESS FOR PURIFYING CRUDE TETRABROMOBISPHENOL SULFONE BY EXTRACTION

This is a continuation-in-part of U.S. Ser. No. 299,495, filed Jan. 23, 1989.

BACKGROUND OF THE INVENTION

1. Field of the Invention

The present invention relates to a procedure for the purification of crude tetrabromobisphenol sulfone (hereinafter referred to as "tetrabromobisphenol S") by using solvent extraction, rather than recrystallization. Tetrabromobisphenol S is tetrabrominated 4,4'-dihydroxydiphenyl sulfone.

2. Description of the Prior Art

It is known in the art to purify certain diphenol compounds by use of recrystallization techniques. For example, German Patent Publication Nos. 2,758,564 to 2,758,566 teach the use of water and an organic co-solvent to purify certain crude diphenol compounds by using recrystallization. Recrystallization techniques are also described in Japanese Patent Publication Nos. 54/119,425 and 62/178,534. The diphenol compounds need to be purified to remove, undesired isomers and other impurities that would impair the physical properties of polymers made from such compounds.

Tetrabromobisphenol S has been found to be a difficult compound to purify. It is usually available as a crude product containing 5-20% or more of tri-, di-, and monobromo sulfones as impurities. Crystallization of the tetrabromo sulfone is difficult since it is insoluble in many solvents and it has a tendency to remain in solution in those cases in which it can be solubilized. One solvent which has been found to work well in a recrystallization procedure producing a good recovery of a high purity product is para-dioxane. However, this solvent is toxic and is not preferred for use for that reason.

SUMMARY OF THE PRESENT INVENTION

The present invention relates to a process for the purification of crude tetrabromobisphenol S by heating that compound in the presence of a quantity of organic solvent which is insufficient to substantially dissolve the compound, followed by removal of the compound from the solvent. Unexpectedly, it has been found that formal recrystallization to obtain a high purity product is not necessary and that simple hot solvent extraction of the crude tetrabromobisphenol S followed by cooling and filtration can give a high purity product.

DETAILED DESCRIPTION OF THE PRESENT INVENTION

The instant invention uses solvent extraction of the crude tetrabromobisphenol S to remove impurities therefrom. Representative solvents of moderate polarity which can be used either alone or in combination in such a technique include the alkoxy alcohols (such as, 2-methoxyethanol, and 1-methoxy-2-propanol), the aliphatic ketones (such as, methyl ethyl ketone and methyl isobutyl ketone), the aliphatic halogenated hydrocarbons (such as, 1,1,2-trichloroethane), the ethers and polyethers (such as dibutyl ether, diglyme, and 1,2-dimethoxyethane), and the esters (such as glycol diacetate, and ethoxyethyl acetate). Most of the solvents listed contain an oxygen atom which may act as a weak Lewis base (electron donor). The extraction procedure is accomplished by heating the tetrabromobisphenol S (e.g., at a temperature of from about 40° to about 200° C.) in the presence of a quantity of organic solvent which is insufficient to substantially dissolve the tetrabromobisphenol S but which is sufficient to extract impurities therefrom. Those solvents generally useful in recrystallizing diphenols can be used in the present process if the amount of solvent is lowered compared to that used in recrystallization and/or the temperature of the solvent is lowered. Generally speaking, a solvent to tetrabromobisphenol S ratio (on a weight basis) of 0.5:1 to 10:1 is contemplated This amount of solvent renders the cooled slurry stirrable and pumpable so filtration, for example, is possible. The tetrabromobisphenol S can be easily removed from the resulting mixture by filtration and, if desired, can be washed with some additional solvent. It is then appropriately dried to form the desired purified tetrabromobisphenol S.

If the solvent that is chosen is also insoluble in water, the crude tetrabromobisphenol S, if wet with water, can be simultaneously dried and purified by azeotropically removing water from the treated tetrabromobisphenol S composition.

The present invention is further illustrated by the Examples which follow.

EXAMPLES 1-12

The general procedure for solvent extraction of tetrabromobisphenol S (TBBS) was to boil the solid for thirty to sixty minutes with at least enough solvent to give a stirrable suspension. The resulting mixture was filtered hot (about 80° C.) or cold (about 25° C.), washed with a little more solvent, and the solid was dried for several hours at 80° C./1 mm. Assays were done by high pressure liquid chromatography (external standard), and the results are shown in the following table.

| Amount TBBS (g) | Purity Initial (wt %) | Purity Final (wt %) | Recovery (g/wt %) | Solvent | Volume (ml) | Filtration (Hot/Cold) |
|---|---|---|---|---|---|---|
| 2 | 86.3 | 94.9 | 1.42/71 | ME | 3 | C |
| 2 | 86.3 | >99 | 0.93/46 | ME | 8 | C |
| 10 | 90.4 | 95.5 | 8.6/86 | ME | 12 | C |
| 5 | 90.4 | 98.6 | 4.3/86 | MP | 6 | H |
| 50 | 94.4 | 96.8 | 46.4/93 | MP | 30 | C |
| 0.5 | 86.3 | >99 | 0.3/60 | DME | 1 | C |
| 1 | 86.3 | 96.7 | 0.73/73 | MEK | 2 | C |
| 2 | 86.3 | 95.3 | 1.6/80 | MEK | 3.5 | C |
| 5 | 90.4 | 96.5 | 4.7/94 | MIBK | 8 | H |
| 2 | 86.3 | 88.0 | 1.93/96 | TCE | 2 | C |
| 2 | 86.3 | 91.7 | 1.71/85 | TCE | 6 | H |
| 20 | 90.4 | 94.9 | 19.2/96 | TCE | 50 | H | solvent key:
ME = 2-methoxyethanol
MP = 1-methoxy-2-propanol
DME = 1,2-dimethoxyethane
MEK = methyl ethyl ketone
MIBK = methyl isobutyl ketone
TCE = 1,1,2-trichloroethane

EXAMPLE 13

A wet cake of crude tetrabromobisphenol S (TBBS) weighing 155 lb (about 85 lb dry weight and 90.5% purity) was charged to a 100 gal reactor containing 210 lb of methyl isobutyl ketone (MIBK). The slurry was refluxed, and water was removed azeotropically over a period of six hours. The mixture was then cooled to 30.C, filtered and was washed with about 75 lb MIBK, followed by 220 lb of water. The wet cake was dried at 65° C./20 mm to give 65 lb of white TBBS of 99% assay by high pressure liquid chromatography.

COMPARATIVE EXAMPLES 14-38

This Example illustrates, for comparative purposes, the attempts to recrystallize tetrabromobisphenol S (TBBS) using a variety of solvents. The purity of the crude TBBS used was 84.5 wt %.

| Solvent | Vol (ml) | Temp (°C.) | Wt TBBS (gm) | TBBS Recovery (wt %) | Purity (wt %) |
|---|---|---|---|---|---|
| Dimethylformamide | 1.0 | 153 | 0.5 | 13 | — |
| Cyclohexanone | 1.1 | 155 | 0.5 | Very poor | — |
| Cyclopentanone | 1.6 | 130 | 0.5 | Very poor | — |
| 2-methoxyethanol | 2.3 | 120 | 0.5 | 28 | — |
| 2-ethoxyethanol | 2.5 | 135 | 0.5 | 34 | — |
| Diglyme | 3.4 | 161 | 0.5 | 0 | — |
| Acetylacetone | 3.7 | 135 | 0.5 | Poor | — |
| Tetrahydrofurfuryl alcohol | 9.7 | 178 | 5.0 | 28 | 96.2* |
| Sulfolane | 12.0 | 150 | 5.0 | 84 | 94.3** |
| Dioxane | 30 | 101 | 5.0 | 78 | 97.7*** |

*a white solid was produced.
**a grey solid was produced.
***crystallized as white needles of 1:1 dioxane/TBBS.

The following solvents were judged unsuitable for crystallization because the TBBS was either insoluble in them or was more poorly soluble than the solvents listed above: methyl ethyl ketone; methyl isopropyl ketone; glyme (1,2-dimethoxyethane); 1-methoxy-2-propanol; diethyl carbonate; butyronitrile; nitromethane; ethanol; isobutyl alcohol; chloroform; 1,2-dichloroethane; 1,1,2-trichloroethane; toluene; and dibutyl ether.

The Comparative Examples illustrate that, in most recent cases, TBBS either cannot be satisfactorily recovered from solvents into which it can be solubilized (the first group of solvents) or it cannot be solubilized in the first place (the second group of solvents).

The foregoing Examples should be not construed in a limiting sense since it is being provided to illustrate certain embodiments of the present invention. The scope of protection that is sought is set forth in the claims which follow.

I claim:
1. A process for the purification of a crude tetrabromobisphenol S composition which comprises heating the composition in the presence of a quantity of substantially organic, moderately polar solvent insufficient to substantially dissolve the tetrabromobisphenol S, which solvent removes impurities from the crude composition, followed by removal of the tetrabromobisphenol S from the solvent.
2. A process as claimed in claim 1 wherein the heating, is performed at a temperature of from about 40° C. to about 200° C.
3. A process as claimed in claim 1 wherein the heating is performed at a temperature of about 40° C. to about 200° C. using a solvent to composition weight ratio of about 0.5:1 to about 10:1.
4. A process as claimed in claim 1 wherein the tetrabromobisphenol is removed from the solvent by filtration.
5. A process as claimed in claim 3 wherein the tetrabromobisphenol is removed from the solvent by filtration.
6. A process as claimed in claim 1 wherein the solvent is an alkoxy alcohol.
7. A process as claimed in claim 3 wherein the solvent is an alkoxy alcohol.
8. A process as claimed in claim 1 wherein the solvent is an aliphatic ketone.
9. A process as claimed in claim 3 wherein the solvent is an aliphatic ketone. 1
10. A process as claimed in claim 1 wherein the solvent is an aliphatic halogenated hydrocarbon.
11. A process as claimed in claim 3 wherein the solvent is an aliphatic halogenated hydrocarbon.

* * * * *